United States Patent [19]
Hochrainer et al.

[11] Patent Number: 6,150,418
[45] Date of Patent: Nov. 21, 2000

[54] ACTIVE SUBSTANCE CONCENTRATE WITH FORMOTEROL, SUITABLE FOR STORAGE

[75] Inventors: Dieter Hochrainer; Bernd Zierenberg, both of Bingen am Rhein, Germany

[73] Assignee: Boehringer Ingelheim Pharma KG, Ingelheim, Del.

[21] Appl. No.: 09/416,474

[22] Filed: Oct. 12, 1999

[30] Foreign Application Priority Data

Oct. 17, 1998 [DE] Germany .............. 198 47 969

[51] Int. Cl.⁷ .................................... A61K 31/16

[52] U.S. Cl. ............................................. 514/630

[58] Field of Search ............................. 514/630

[56] References Cited

U.S. PATENT DOCUMENTS 4,814,161 3/1989 Jinks et al. .................. 424/45
5,795,564 8/1998 Aberg et al. ................ 424/45

FOREIGN PATENT DOCUMENTS 9747286 12/1997 WIPO .

*Primary Examiner*—Theodore J. Criares
*Assistant Examiner*—Jennifer Kim
*Attorney, Agent, or Firm*—R. P. Raymond; M-E M. Devlin; A. R. Stempel

[57] ABSTRACT

The present invention relates to a formoterol active substance concentrate suitable for storage, in the form of a solution or suspension for use in inhalers for inhalation or nasal therapy.

22 Claims, No Drawings

ACTIVE SUBSTANCE CONCENTRATE WITH FORMOTEROL, SUITABLE FOR STORAGE

The present invention relates to a propellant-free, active substance concentrate suitable for storage containing formoterol, for use in inhalers for inhalation or nasal therapy.

Formoterol is an anilide of formula I derived from adrenaline and is used as a $\beta_2$-stimulator in inhalation therapy of respiratory diseases, particularly for the treatment of bronchial asthma. In patients with reversible obstructive respiratory diseases, formoterol has a bronchodilatory effect. Only 1–3 minutes after inhalation the effect sets in and the bronchodilatory effect is still significantly present after 12 hours. Formoterol inhibits the release of leukotrienes and other messenger substances involved with inflammation, such as histamines. In addition, formoterol may bring about a hyperglycaemic activity.

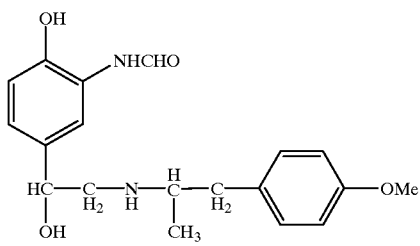

Formula I

In the past it has been found that liquid aerosol formulations of formoterol are not suitable for use in inhalers intended for ambulatory inhalation treatment since formoterol cannot be stored in a sufficiently stable manner in solution to guarantee the pharmaceutical quality of the formulation over lengthy periods of time. For this reason, formoterol has previously only been used in powder form for inhalation therapy.

The present invention relates to a liquid active substance concentrate containing formoterol in the form of its free base or in the form of one of the pharmacologically acceptable salts or addition products (adducts) thereof as active substance. The preferred salt is formoterol fumarate whilst the preferred addition product is a hydrate of formoterol. In the wider context of this specification, the term formoterol refers both to the free base according to formula I and also to salts and other addition products of formoterol unless otherwise specified or clearly stated in the context.

The active substance concentrate according to the invention may be converted, by diluting with a pharmacologically acceptable liquid which optionally contains pharmaceutical adjuvants and additives, into a pharmaceutical preparation (aerosol formulation) which is converted by means of a nebuliser into an inhalable aerosol.

The invention therefore also relates to the use of an active substance concentrate of this kind in inhalation therapy.

The active substance concentrate according to the invention refers to solutions or suspensions in which formoterol is dissolved or suspended in highly concentrated form in a pharmacologically suitable fluid and which are characterised in that the active substance, formoterol, can be stored therein for a period from several months possibly up to several years without any deterioration in the pharmaceutical quality.

The term "active substance concentrate" denotes a solution or suspension of an active substance in which the active substance, formoterol, is present in highly concentrated form in a pharmacologically acceptable liquid as a solution or suspension. Suspensions are preferred as they have proved particularly stable on storage.

The term "highly concentrated" means a concentration of the active substance which is usually too high to enable the corresponding solution or suspension to be used therapeutically for inhalation without being diluted. According to the invention the formoterol concentration in the active substance concentrate is between 10 mg/ml and 500 mg/ml. Preferably, the minimum concentration is at least 75 mg/ml. Preferred concentrations are between 100 mg/ml and 400 mg/ml, particularly between 250 mg/ml and 350 mg/ml. The concentration data relate to mg of free base formoterol per ml of active substance concentrate. In the case of formoterol salts or the addition compounds thereof, the concentration data should be converted according to the free base.

The term "pharmacologically suitable fluid" for the purposes of the present invention means a solvent or suspension agent which is not a liquefied propellant gas. Polar fluids are preferred, particularly protic fluids.

Examples of polar solvents or suspension agents are e.g. dimethylsulphoxide or compounds which contain hydroxyl groups or other polar groups, e.g. water or alcohols—particularly ethanol, isopropylalcohol, glycols, especially propyleneglycol, polyethyleneglycol, polypropyleneglycol, glycolether, glycerol, polyoxyethylene alcohols and polyoxyethylene fatty acid esters etc.

Examples of protic liquids, which are the most preferred solvents or suspension agents in the context of the invention, are water, aqueous saline solutions with one or more pharmacologically acceptable salt(s), ethanol or a mixture thereof.

In the case of aqueous ethanol mixtures, the ratio by volume of ethanol to water or to the aqueous saline solution is between 5:95 and 99:1, preferably between 40:60 and 96:4, most preferably between 75:25 and 96:4. A particularly preferred ratio is between 40:60 and 60:40.

For a saline solution as the solvent or suspension agent or as a component thereof, particularly suitable salts are those which display no or only negligibly little pharmacological activity after administration. Saline solutions are preferably used for suspension concentrates. The addition of the salt significantly reduces the dissolving power of water for the active substance or substances, so as to achieve a stabilising effect on the suspended particles. If desired, saturated saline solutions may be used. The quantity of salt depends on the precise composition of the solvent or suspension agent and its ability to dissolve the active substance. Formoterol should be present in dissolved form in an amount of less than 0.5% by weight, preferably less than 0.1% by weight, in aqueous formoterol suspensions in the sense of the active substance concentrate according to the invention, these amounts being based on the total amount (weight) of formoterol. However, if the amount of dissolved material is above the specified levels, it can be reduced to below these levels by the addition of salt.

As a rule, the solubility can be halved by the addition of salt, and in some cases reduced to one fifth or even less.

Preferred are saline solutions with a salt content of up to 50% by weight, especially up to 20% by weight.

Both inorganic and organic salts may be used as the salts. Inorganic salts such as sodium chloride, alkali metal or ammonium halogen salts are preferred. Sodium chloride is particularly preferred. Suitable organic salts are, for example, the sodium, potassium or ammonium salts of the following acids: ascorbic acid, citric acid, malic acid, tartaric acid, maleic acid, succinic acid, fumaric acid, acetic acid, formic acid and/or propionic acid.

Cosolvents may be added to the solvent or suspension agent. Co-solvents are suitable for increasing the solubility of additives and optionally the formoterol.

Preferred cosolvents are those which contain hydroxyl groups or other polar groups, for example alcohols—especially isopropyl alcohol, glycols—especially propylene glycol, polyethylene glycol, polypropylene glycol, glycol ether, glycerol, polyoxyethylene alcohols and polyoxyethylene fatty acid esters, provided that these are not already used as the solvent or suspension agent.

Other excipients and additives may also be added to the active substance concentrate according to the invention.

The term excipients and additives in this context denotes any pharmacologically suitable and therapeutically useful substance which is not an active substance but can be formulated together with the formoterol in the pharmacologically suitable solvent or suspension agent in order to improve the qualitative properties of the active substance concentrate or the pharmaceutical preparation which is to be obtained by dilution ready for inhalation. Preferably, these substances have no pharmacological activity or, in the context of the desired therapy, no appreciable or at least no undesirable pharmacological activity. The excipients and additives include, for example, surfactants for stabilising suspensions, other stabilisers, complexing agents, antioxidants and/or preservatives which prolong the duration of use of the finished pharmaceutical formulation, flavourings, vitamins, antioxidants and/or other additives known in the prior art.

As surfactants the active substance concentrate may contain, for example, soya lecithin, oleic acid, sorbitan esters such as sorbitan trioleate or other surfactants known from the prior art in the usual concentrations.

It has been found that addition of an organic or inorganic acid, preferably in combination with a complexing agent, leads to improvement in the stability (shelf life) of some solutions or suspensions containing formoterol, particularly if they contain ethanol as solvent.

Examples of inorganic acids which are preferred in this respect are: hydrochloric acid, nitric acid, sulphuric acid and/or phosphoric acid. Examples of especially suitable organic acids are: ascorbic acid, citric acid, malic acid, tartaric acid, maleic acid, succinic acid, fumaric acid, acetic acid, formic acid and/or propionic acid, etc. The preferred acids are hydrochloric acid and/or fumaric acid.

The concentration of acid is selected so that the active substance concentrate has a pH of between 2.0 and 7.0, preferably between 4.0 and 6.0 and most preferably between 4.5 and 5.5.

Examples of complexing agents which may be used include EDTA (ethylenediaminetetraacetic acid, or a salt thereof, such as the disodium salt), citric acid, nitrilotriacetic acid and the salts thereof. EDTA is preferred.

Preservatives can be used to protect the concentrate from contamination with pathogenic germs. Those preservatives which are known in the prior art are suitable, especially benzalkonium chloride or benzoic acid, or benzoates such as sodium benzoate.

Suitable antioxidants are the known pharmacologically acceptable antioxidants, especially vitamins or provitamins, as present in the human body, e.g. ascorbic acid or vitamin E.

If the formoterol is present in the active substance concentrate according to the invention as a suspension, the particles are preferably formulated in a particle size of up to 20 :m, preferably up to 10 :m and especially preferably up to 5 :m.

Suspensions are most preferred as the active substance concentrate.

The active substance concentrate according to the invention has the advantage that formoterol can be formulated in such a way as to remain stable over a fairly long period of time. It is not necessary for the concentrate to correspond to the composition of the finished pharmaceutical preparation, apart from the concentration of the active substance. For example, the pH of the concentrate may differ substantially from the pH of the pharmaceutical preparation which is to be administered, if this ensures more stable storage of formoterol.

The active substance concentrate according to the invention is not usually suitable as such for direct medicinal use, particularly for inhalation. As already explained, use of the active substance concentrate comprises converting it into a pharmaceutical preparation (aerosol formulation). The term "pharmaceutical preparation" denotes a formulation of a pharmaceutical substance suitable for inhalation wherein a pharmaceutical substance or mixture of substances can be administered in the required and/or recommended concentration.

The pharmaceutical preparation is preferably such that it can be administered by inhalation using a suitable nebuliser.

A preferred method of converting the active substance concentrate into a pharmaceutical preparation suitable for administration is by diluting the active substance concentrate according to the invention with a pharmacologically suitable solvent or suspension agent.

In order to obtain the formulation for administration, the formoterol active substance concentrate is diluted to 0.9 mg/ml to 1.5 mg/ml, for example, with the diluent.

Preferred solvents or suspension agents for the dilution are propellant-free liquids, preferably polar, more particularly protic liquids. It should be pointed out here that the individual components or ingredients of the diluent are defined as specified in connection with the active substance concentrate, in so far as these components or ingredients were described there or unless otherwise stated.

Particularly preferred diluents are water, aqueous saline solutions with one or more pharmacologically acceptable salts, ethanol or a mixture thereof. In the case of aqueous ethanol mixtures, the ratio by volume of ethanol to water or to the aqueous saline solution is between 5:95 and 99:1, preferably between 40:60 and 96:4, most preferably between 75:25 and 96:4. A particularly preferred ratio is between 40:60 and 60:40.

It is neither obvious nor necessary for the diluent to be identical to the solvent or suspension agent of the active substance concentrate. If desired, the latter may also contain only one or a few constituents of the diluent.

It should be expressly pointed out here that the cosolvents and/or excipients or additives and/or active substances mentioned above in connection with the active substance concentrate according to the invention may also or only be dissolved or suspended in the diluent.

Preferred embodiments of the diluent contain preservatives and/or complexing agents.

Optionally, the diluent may contain a buffer substance, e.g. trisodium phosphate, disodium hydrogen phosphate, sodium dihydrogen phosphate, Na-EDTA, EDTA, mixtures thereof and other substances known from the prior art. Preferred substances are sodium dihydrogen phosphate, disodium hydrogen phosphate, trisodium hydrogen phosphate, potassium dihydrogen phosphate, potassium hydrogen phosphate, tripotassium hydrogen phosphate, and mixtures thereof. Buffer substances are particularly beneficial when the active substance concentrate suitable for storage according to the invention has a pH which differs significantly from that which is desired for the application, e.g. when this increases the stability of the active substance during storage. In this case the buffer substance is present in the diluent in a concentration such that, after mixing the active substance concentrate with the diluent, an aerosol formulation suitable for administration is obtained with the desired pH, preferably between 2.0 and 7.0, particularly between 4.0 and 6.0, most preferably between 4.5 and 5.5.

In a preferred embodiment, the pharmaceutical preparation contains a complexing agent which is preferably selected from a complexing agent mentioned in connection with the active substance concentrate. The quantity of complexing agent is up to 100 mg/100 ml, preferably up to 50 mg/100 ml. The preferred complexing agent is EDTA.

The pharmaceutical preparation which is to be administered together with the active substance concentrate determines the precise composition of the diluent.

Neither the active substance concentrate suitable for storage according to the invention nor the pharmaceutical preparation for administration obtained by dilution contains a propellant.

Preferably, the mixing takes place at ambient temperature and under normal pressure. One advantage of the active substance concentrate according to the invention is that it can be converted by dilution into a therapeutically effective formulation and/or one which is suitable for use in a nebuliser within a very short time, e.g. within a few minutes or possibly a few seconds. The mixing can also be done by patients, who generally have no pharmaceutical knowledge.

For use in inhalation therapy, the active substance concentrate according to the invention is preferably diluted by means of a suitable nebuliser before the first application and the pharmaceutical preparation obtained is then atomised by the nebuliser.

Suitable nebulisers in this context are those which can nebulise liquid formulations containing no propellant. Preferred nebulisers are, for example, inhalers or high pressure atomisers as disclosed in WO91/14468 "Atomizing Device and Methods" or WO97/12687, particularly those described by FIGS. 6a and 6b, to which reference is hereby made in its entirety. In nebulisers of this kind, pharmaceutical preparations intended for administration in the form of solutions are generally preferred to suspensions.

Preferably, the active substance concentrate according to the invention and the diluent are stored separately in a container which is suitable for inhalers and which is so designed that the two components are automatically mixed together as the container is inserted in the nebuliser or immediately before the first use, so to speak in situ. Containers which are preferred for this purpose are disclosed for example in PCT/EP95/03183, in WO97/39831 and particularly FIGS. 1, 2, 2a or 3b therein or in the German Patent Application bearing the serial number 198 47 968.9 and particularly the cartridges illustrated in FIGS. 1 to 11 therein, especially FIG. 3, to which reference is hereby made in their entirety. These containers are particularly suitable for use in a high pressure atomiser of the type described above.

Two or more separate chambers might be formed in such a container, the active substance concentrate according to the invention being stored in at least one of the chambers while the diluent is stored in another chamber. The container is designed so that the two components stored separately can be mixed together simply by inserting the container in the inhaler designed for this purpose. The quantity of the two components is such that after the two components have been mixed together an aerosol formulation is obtained in which the active substance or substances is or are concentrated to such an extent that the recommended therapeutic dose can be administered by a single spray or just a few sprays of the appropriate nebuliser. Within the scope of the present description, a method of this kind or a similar method for producing the aerosol formulation which is to be administered might be designated an "in situ" method or a "quasi in situ" method if the user is not required to take any measures going beyond or preceding the normal measures for operating an inhaler and using the aerosol formulation by means of the inhaler.

For the purpose of storage in the abovementioned cartridge, in preferred embodiments, the quantity of the active substance concentrate suitable for storage according to the invention is chosen so as to correspond to a volume of from 0.001 up to about 0.05 ml, preferably from 0.001 to 0.02 ml.

In addition to those described, other containers may also be used to store the formulation according to the invention.

Of course, the dilution may also be carried out differently with a pharmacologically acceptable diluent, e.g. by mixing the diluent with the active substance concentrate in an open vessel or by some other method.

EXAMPLES

Example 1

5 mg of formoterol (particle size: 5 μm) are formulated as a suspension with 0.015 ml of water for storage. A pH of 5.0 is obtained by the addition of fumaric acid.
Preparation of the pharmaceutical preparation for administration by inhalation:

For administration by inhalation, the suspension is diluted with 4.5 ml of a 1:1 solution of water/ethanol (v/v), the diluted solution containing 0.45 mg of benzalkonium chloride and 2.25 mg of Na-EDTA and being adjusted to a pH of 5.0 using HCl.

The concentration of the active substance concentrate is about 300 times higher than the concentration of the solution to be administered.

Example 2

5 mg of formoterol (particle size: 5 μm) are formulated as a suspension for storage with 0.015 ml of a 20% by weight aqueous NaCl solution. The pH is adjusted to 5.0 by the addition of fumaric acid.
Preparation of the pharmaceutical preparation for administration by inhalation:

For inhalation, the suspension is diluted with 4.5 ml of a 1:1 solution of water/ethanol (v/v), the dilute solution containing 0.45 mg of benzalkonium chloride and 2.25 mg of Na-EDTA and being adjusted with HCl to a pH of 5.0.

The concentration of the active substance concentrate is around 300 times greater than the concentration of the solution to be administered.

Example 3

In an aqueous solution with a pH of 5.0, formoterol breaks down to 10% at 40° C. within only 3 months. In a comparable suspension, no breakdown of any kind can be observed even after 6 months' storage at 40° C.

What is claimed is:

1. Propellant-free active substance concentrate suitable for storage containing formoterol in the form of its free base, one of the pharmacologically acceptable salts thereof or one of the addition products thereof as the active substance, in a pharmacologically acceptable solvent or suspension agent, wherein the concentration of formoterol is between about 75 mg/ml and about 500 mg/ml.

2. Active substance concentrate according to claim 1, characterised in that the concentration of formoterol is between about 100 mg/ml and about 400 mg/ml.

3. Active substance concentrate according to claim 2, characterised in that the concentration of formoterol is between about 250 mg/ml and about 350 mg/ml.

4. Active substance concentrate according to claim 1, characterised in that the solvent or suspension agent is polar.

5. Active substance concentrate according to claim 4, characterised in that the solvent or suspension agent is a protic liquid.

6. Active substance according to claim 1, characterised in that the solvent or suspension agent is water, an aqueous saline solution, ethanol or a mixture thereof.

7. Active substance concentrate according to claim 6, characterised in that the aqueous saline solution is a sodium chloride solution.

8. Active substance concentrate according to claim 1, characterised in that the formoterol is dissolved.

9. Active substance concentrate according to claim 1, characterised in that the formoterol is suspended in water or an aqueous saline solution.

10. Active substance concentrate according to claim 1, characterised in that the formulation contains a surfactant selected from sorbitan ester, oleic acid and lecithin.

11. Active substance concentrate according to claim 1, characterised in that the active substance concentrate contains a pharmacologically acceptable acid.

12. Active substance concentrate according to claim 11, characterised in that the acid is selected from the group consisting of hydrochloric, nitric, sulphuric, posphoric, ascorbic, citric, malic, tartaric, maleic, fumaric, succinic, acetic, formic and propionic.

13. Active substance concentrate according to claim 12, characterised in that the acid is hydrochloric or fumaric.

14. Active substance concentrate according to claim 1, characterised in that the pH of the active substance concentrate is between about 2.0 and about 7.0.

15. Active substance concentrate according to claim 14, characterised in that the pH of the active substance concentrate is between about 4.0 and about 6.0.

16. Active substance concentrate according to claim 15, characterised in that the pH of the active substance concentrate is between about 4.5 and about 5.5.

17. Active substance concentrate according to claim 1, characterised in that the active substance concentrate contains a preservative, an antioxidant or a complexing agent.

18. Active substance concentrate according to claim 1, characterised in that the formulation contains one or more additional inhalatively active pharmaceutical substances.

19. Active substance concentrate according to claim 18, characterised in that the additional inhalatively active pharmaceutical substance is selected from the group consisting of betamimetics, antichlolinergics, antiallergics, leukotriene antagonists, steroids and mixtures thereof.

20. Active substance concentrate suitable for storage, containing formoterol as active substance, characterised in that formoterol is present as a suspension in water in a concentration of between about 250 mg/ml and about 350 mg/ml and in that the active substance concentrate is adjusted to a pH of about 4.5 to about 5.5 and is in the form of a pharmacologically acceptable salt in an amount such that the formoterol is dissolved to an extent of less than about 0.5% (w/w).

21. Active substance concentrate according to claim 20, characterised in that the formoterol is dissolved to an extent of less than about 0.1% (w/w).

22. Formulation of a solution for inhalation therapy, containing a solvent mixture of ethanol/water which is adjusted to a pH of about 4.5 to about 5.5, dissolved formoterol in a concentration of about 0.9 to about 1.5 mg/ml based on formoterol, a preservative in a pharmacologically acceptable amount and Na-EDTA in a pharmacologically acceptable amount.

* * * * *